United States Patent
Farrell et al.

(10) Patent No.: US 8,388,983 B2
(45) Date of Patent: Mar. 5, 2013

(54) FILM COATINGS CONTAINING FINE PARTICLE SIZE DETACKIFIERS AND SUBSTRATES COATED THEREWITH

(75) Inventors: Thomas P. Farrell, Warrington, PA (US); Jason Teckoe, Lansdale, PA (US); Barry Friend, Dartford (GB); Scott Gulian, Lansdale, PA (US)

(73) Assignee: BPSI Holdings, LLC, Wilmington, DE (US)

( * ) Notice: Subject to any disclaimer, the term of this patent is extended or adjusted under 35 U.S.C. 154(b) by 114 days.

(21) Appl. No.: 12/769,197

(22) Filed: Apr. 28, 2010

(65) Prior Publication Data

US 2010/0291159 A1 Nov. 18, 2010

Related U.S. Application Data

(60) Provisional application No. 61/177,380, filed on May 12, 2009, provisional application No. 61/300,132, filed on Feb. 1, 2010.

(51) Int. Cl.
- *A61K 47/32* (2006.01)
- *A61K 9/00* (2006.01)
- *B05D 7/00* (2006.01)
- *C08K 5/41* (2006.01)

(52) U.S. Cl. ..... 424/400; 427/2.14; 524/156; 514/772.6

(58) Field of Classification Search ............ 424/400
See application file for complete search history.

(56) References Cited

U.S. PATENT DOCUMENTS

| | | |
|---|---|---|
| 4,725,441 A | 2/1988 | Porter et al. |
| 4,828,841 A | 5/1989 | Porter et al. |
| 5,330,759 A | 7/1994 | Pagay et al. |
| 5,567,768 A | 10/1996 | Amici et al. |
| 5,733,575 A * | 3/1998 | Mehra et al. ............. 424/480 |
| 5,885,617 A | 3/1999 | Jordan |
| 6,039,976 A * | 3/2000 | Mehra et al. ............. 424/480 |
| 6,207,199 B1 | 3/2001 | Allen et al. |
| 6,420,473 B1 | 7/2002 | Chittamuru et al. |
| 6,448,323 B1 * | 9/2002 | Jordan et al. ............. 524/451 |
| 6,468,561 B1 | 10/2002 | Grillo et al. |
| 6,579,953 B1 | 6/2003 | Gotsche et al. |
| 2003/0232082 A1 * | 12/2003 | Li et al. ............. 424/473 |
| 2006/0134216 A1 * | 6/2006 | Farrell et al. ............. 424/472 |
| 2006/0147522 A1 | 7/2006 | Olmstead et al. |
| 2006/0229383 A1 * | 10/2006 | Noami et al. ............. 523/160 |
| 2007/0134324 A1 | 6/2007 | Messadek |
| 2008/0254112 A1 | 10/2008 | Klokkers et al. |
| 2009/0004292 A1 | 1/2009 | Kumar et al. |
| 2010/0273884 A1 | 10/2010 | Clouatre et al. |

FOREIGN PATENT DOCUMENTS

WO 2006111980 10/2006

OTHER PUBLICATIONS

International Search Report and Written Opinion issued in PCT/US2010/32749 and dated Jun. 29, 2010.
W. Anderson, et al., Coating of Pharmaceutical Tablets: ..., J. Pharm. Pharmac., vol. 18. pp. 783-794, 1966.

* cited by examiner

*Primary Examiner* — Richard Schnizer
*Assistant Examiner* — Audrea Buckley
(74) *Attorney, Agent, or Firm* — Lucas & Mercanti, LLP

(57) ABSTRACT

The present invention is directed to film coating compositions for use on oral dosage forms such as compressed tablets and other orally-ingestible substrates which contain a fine particle size detackifier. The film coating compositions can be applied either directly to a substrate or after the substrate has been coated with a subcoat. In preferred aspects, the polymer is either polyvinyl alcohol or a copolymer of polyvinyl alcohol. Aqueous suspensions comprising the inventive film coating compositions, methods of applying the coatings to substrates and the coated substrates themselves are also disclosed.

19 Claims, No Drawings

FILM COATINGS CONTAINING FINE PARTICLE SIZE DETACKIFIERS AND SUBSTRATES COATED THEREWITH

CROSS REFERENCE TO RELATED APPLICATION

This application claims the benefit of priority under 35 U.S.C. 119(e) from U.S. Patent Application Ser. No. 61/177,380 filed May 12, 2009, and U.S. Patent Application Ser. No. 61/300,132, filed Feb. 1, 2010, the contents of each of which are incorporated herein by reference.

1. FIELD OF THE INVENTION

The present invention relates to film coating formulations which contain fine particle size, waxy detackifiers. The invention also relates to pharmaceutical substrates having such film coatings and methods of preparing the same.

2. DESCRIPTION OF THE PRIOR ART

The use of detackifiers in film coating compositions is described in the prior art for both immediate release and enteric film coating applications. The use of self-emulsifying glyceryl monostearate (SE-GMS) as an anti-tack agent in immediate-release film coating formulations based on polyvinyl alcohol (PVA) is described in WO2006111980 and WO2006111981. In these applications, a hot water dispersion process is described to enable melting of the GMS and complete dispersion of the film coating comprising SE-GMS prior to coating onto tablets. Consequently, these aqueous film coating dispersions are heated to 70-90° C. It is further added, specifically, in WO2006111981 that an essential feature is the use of hot water for reconstituting the dry moisture barrier coating composition. The glyceryl monostearate can function as an anti-tack agent and as a plasticizer only after it melts. Since the state of the art in the pharmaceutical industry is that film coating formulations are dispersed in water at ambient temperatures, the heating steps described in the '980 and '981 applications represent an additional, time-consuming and inconvenient step for the artisan making film coating dispersions. Temperatures of 70-90° C. may also cause degradation or volatilization of some components typically included in film coating formulations such as flavorants and plasticizers.

WO2004012718 describes the use of an anti-sticking agent in film coatings for modified release whereby the coating formulation consists of acrylic polymer latex (NE30D) and an anti-sticking agent (GMS) as well as a surface active agent. In contrast to the current invention, the '718 application describes the use of hot water, at a temperature of 60-63° C., to solubilize the GMS in a solution containing the surface active agent to generate a stable liquid dispersion with fine particle size before addition to the acrylic polymer latex. This method of employing GMS—i.e. dispersing in hot water—is disadvantageous, because it represents an additional, time-consuming step and also may contribute to the instability or volatilization of other additives such as plasticizers and flavorants, which may be beneficial to the film coating.

3. SUMMARY OF THE INVENTION

It has been surprisingly found that the use of fine particle size, waxy materials as detackifiers in film coating formulations has provided the ability to generate, in ambient temperature water, a uniform film coating dispersion. Use of the inventive film coating results in enhanced coating process reliability (reduced gun blockages), increased coating process productivity (increased fluid delivery rate), improved product uniformity and appearance as well as comparable or better moisture barrier performance of formulated coating systems when compared to that of the prior art.

The present invention relates to the development of a fully-formulated film coating system utilizing a fine particle size, as defined hereinbelow, detackifier based on a waxy material, which in some preferred aspects is practically insoluble in ambient temperature water. The invention further relates to aqueous dispersions comprising the fine particle sized waxy detackifier, methods of preparing the same by dispersing the film coating materials (system) in ambient temperature water.

Waxy materials that are practically insoluble in water at ambient temperature (i.e. solubility of less than about 0.1 g/mL) are typically supplied as large flakes, beads or as solid waxes that are often inconvenient to work with in these forms. It has been found that waxy detackifiers may be more conveniently used in film coating formulations if their particle sizes are reduced. One method of achieving particle size reduction is by first melting a waxy material of relatively large particle size and then cooling the corresponding liquid in atomized droplet form to produce smaller particles. Other means of particle size reduction for rendering the waxy materials to the median particle sizes set forth herein known to those of ordinary skill are also contemplated for use herein.

Film coatings comprising fine particle size, waxy materials as detackifiers may be dispersed in water at ambient temperature, and the resulting film coating dispersions may be applied to orally-ingestible substrates using standard film coating equipment without encountering film coating process issues, such as spray nozzle blockage or residue in the coating pan associated with undispersed waxy materials.

In one aspect of the invention, there are provided dry powder film coating compositions for the pharmaceutical and related arts. The dry powder film coating compositions include one or more polymers, fine particle sized waxy detackifiers, which are practically insoluble in water at ambient temperatures, and optionally plasticizers, glidants, pigments and other additives commonly used in film coating formulations. In preferred aspects of this invention, the fine particle size detackifiers are waxy materials, and also have a median particle size of less than about 150 microns, preferably less than about 100 microns and most preferably less than about 50 microns. In addition, the preferred fine particle size detackifiers have d (0.9) values of not more than 250 microns.

In another aspect of the invention, there are provided aqueous dispersions of the film coating compositions described above. The dispersions preferably contain from about 10 to about 25% non-water ingredients content. Still further aspects include methods of coating orally-ingestible substrates with the coating suspension as well as the coated substrates prepared by these methods.

In the preferred aspects of this invention, immediate release film coatings are identified that have water vapor transmission rates of about 6-9 grams water/day/100 in$^2$, which is comparable to that obtained in U.S. Pat. No. 5,885,617, and with a maximum fluid delivery rate in excess of 25 g/min in a 15" fully perforated pan with no coating issues such as gun blockages and without the need to use hot water to reconstitute the coating solution. Preferably, the film coating has a water vapor transmission rate (WVTR or also known as moisture vapor transmission rate-MVTR) of less than about 9 g H$_2$O/day/100 in$^2$. This combination of properties for an immediate release film coating system is clearly advantageous over the prior art and existing marketed products.

4. DETAILED DESCRIPTION OF THE INVENTION

For purposes of the present invention, the following terms are given further clarification as to their meanings:
"orally-ingestible substrate" shall be understood to mean any pharmaceutically acceptable dosage form, e.g. tablet, capsule, caplet, etc. or any other veterinary or confectionery product capable of being taken via the oral route of administration;
"dry powder" shall be understood to mean powders which are relatively dry to the touch rather than powders which are essentially without moisture content; and
"ambient temperature" shall be understood to mean temperatures generally in the range of from about 20° C. (68° F.) to about 30° C. (86° F.)+/−3° C.

The inventive film coating compositions comprise one or more polymers, fine particle size detackifiers and optionally plasticizers, glidants, pigments and surfactants.

The polymer may be any of the commonly used film formers in the film coating art. These may include hypromellose (hydroxypropylmethyl cellulose), hydroxypropyl cellulose, sodium carboxymethyl cellulose, polyvinyl alcohol (PVA), copolymers based on PVA, polyvinylpyrrolidone-vinyl acetate copolymer (copovidone), polyvinylacetate phthalate, methacrylic acid copolymers and other polymers found useful for immediate or delayed release coatings. A preferred grade of PVA is one prepared by hydrolyzing 86.5 to 89 mol % of the acetate groups on polyvinyl acetate. In a further embodiment of the invention, one grade of polyvinyl alcohol copolymer found useful comprises polyvinyl alcohol, which has a percentage of hydrolysis greater than about 86.5 mol % and preferably in the range of about 86.5 to 89 mol %, onto which has been graft polymerized methyl methacrylate and acrylic acid to give a ratio of PVA-methyl methacrylate-acrylic acid moieties of 80:17.5:2.5. See, for example, US Patent Application Publication No. 2006/0229383, the disclosure of which is incorporated herein by reference. One such commercially available product is sold under the trade name "Povacoat". Additional examples of polyvinyl alcohol copolymers found useful are graft copolymers of polyvinyl alcohol and polyethylene glycol (PEG) such as the PVA-PEG graft copolymer sold under the trade name Kollicoat IR and those described in U.S. Pat. No. 6,579,953. Suitable methacrylic acid copolymers include: poly(methacrylic acid, methyl methacrylate) 1:1 sold, for example, under the Eudragit L100 tradename; poly(methacrylic acid, ethyl acrylate) 1:1 sold, for example, under the Eudragit L100-55 tradename; partially-neutralized poly(methacrylic acid, ethyl acrylate) 1:1 sold, for example, under the Kollicoat MAE-100P tradename; and poly(methacrylic acid, methyl methacrylate) 1:2 sold, for example, under the Eudragit S100 tradename. A suitable methacrylate copolymer is poly(butyl methacrylate, 2-dimethylaminoethyl methacrylate, methyl methacrylate) 1:2:1 sold, for example, under the Eudragit E PO tradename. Preferably, the polymers are micronized to facilitate dissolution into ambient water when forming the aqueous coating solution.

In most embodiments, the total amount of polymer included in the powder mixtures of the present invention is from about 20 to about 80% by weight. In some preferred embodiments, it ranges from about 25 to about 60% and more preferably ranges from about 30 to about 50%.

In most preferred aspects of the invention, the fine particle size detackifiers include waxy materials that are practically insoluble in water (i.e. solubility less than about 0.1 g/mL) at ambient temperatures. A non-limiting list of materials that meet these criteria includes glyceryl monostearate, glyceryl behenate (e.g. Compritol 888 ATO), glyceryl palmitostearate (e.g. Precirol ATO 05), sorbitan esters (e.g. sorbitan monopalmitate—Span 40), stearic acid, palmitic acid, polyoxyethylene alkyl ethers (e.g. Cremophor AG; Brij 52; Brij 72; Volpo S2; and Ethylan 2512), lauroyl polyoxylglycerides (e.g. Gelucire 44/14) and stearoyl polyoxylglycerides (e.g. Gelucire 50/13), ceresin, cetostearyl alcohol, cetyl alcohol, docusate sodium, ethyl maltol, ethylene glycol stearates, glyceryl monooleate, lanolin, myristic acid, petrolatum/lanolin alcohols, polyoxyl 6 stearate, polyoxyl 8 stearate, propylene glycol monostearate, sorbitan tristearate, sodium stearyl fumarate, stearyl alcohol, hydrogenated vegetable oil, carnauba wax, microcrystalline wax and zinc stearate.

In some aspects of the invention, glyceryl monostearate, lauroyl polyoxylglycerides and stearoyl polyoxylglycerides are the most preferred fine particle size detackifiers. Other waxy detackifiers not specifically listed but having the same or substantially the same solubility profile are also contemplated for inclusion herein.

For purposes of the present invention, "fine particle size" shall be understood to mean a median particle size of less than about 150 microns, preferably less than about 100 microns and most preferably less than about 50 microns. In addition, preferred detackifiers have at least 90% of particles with dimensions less than about 250 microns, most preferably less than about 150 microns. Particles with dimensions greater than about 250 microns are much more likely to clog spray guns, which typically have nozzles or apertures of about 1 millimeter. In some other preferred aspects of the invention, the amount of waxy detackifier particles having a particle size of greater than about 150 microns is less than about 7.5% and more preferably less than about 5%. Also, preferred detackifiers should be substantially free of large particles greater than about 600 microns.

In one embodiment, the fine particle size detackifiers are prepared using a spray cooling procedure whereby waxy materials that are practically insoluble in water are heated into a fully liquid state. Then, using a fluid bed apparatus configured for top spray atomization (well known to those of ordinary skill) and using heated compressed air to the spray gun and jacketed fluid lines the liquid is sprayed into the fluid bed air steam causing the atomized material to solidify. The solidified material is formed in a fine particle form, which may be further fractionated into different particle size distributions. Due to the nature of the spray cooling process, the physical form of the fine particle size materials are generally rounded particles or cylindrical agglomerates with rounded form, which aid powder flow and homogeneous distribution throughout a film coating formulation comprising multiple components. The nature and size of the fine particle size material will be dependent on the individual material characteristics, but typically properties can be adjusted to provide the required particle size range through process control of the atomization air pressures, temperature and fluid delivery rates. In addition it may be found to be advantageous to spray cool the practically insoluble material with another ingredient to form a co-processed mixed blend to reduce the potential for the spray cooled material to agglomerate on storage. For example, a surfactant such as sodium lauryl sulfate can be co-processed with the waxy detackifier in amounts of up to about 7%.

In an alternative embodiment, waxy materials, commonly obtained in flake form, may be milled to reduce particle size and subsequently sieved to obtain median particles sizes of less than about 150 microns. Materials of reduced particle size obtained by milling can, however, have varied and irregular shapes. As such, while materials rendered to the desired median particle size can be used in the present invention, spray cooled particles are preferred. If desired, the waxy detackifier particles, however obtained, can be screen or otherwise separated to obtain the preferred median particle size profile.

The detackifier is used principally to reduce the incidence of tablet-to-tablet sticking that can occur during the film coating of pharmaceutical tablets and the like using aqueous suspensions/dispersions based on the inventive compositions. The total amount of detackifier present will depend upon need, but when included can broadly range from about 1 to about 30% by weight. Preferably, the range is from about 2 to about 15% and more preferably from about 4 to about 10% by weight.

In certain embodiments of the invention, plasticizers are advantageously included to enhance film formation. A non-limiting list of suitable plasticizers includes polyethylene glycol, triethyl citrate, glycerin, triacetin and soya lecithin. One preferred plasticizer is triethyl citrate. The preferred use levels for plasticizers such as triethyl citrate are from about 1 to 25%, preferably between about 2-20%, and more preferably between about 4 and about 15%.

A glidant is optionally used to help tablets flow over each other and so generate a smooth surface finish. A preferred glidant is talc. The amount of glidant, when present, will depend upon need, but can broadly range from about 9 to about 50% by weight, preferably, the range is from about 12 to about 40%, and, more preferably, from about 15 to about 30%.

Pigments are also optionally added and may be any food or pharmaceutically approved colors, opacifiers or dyes. For example, the pigments may be aluminum lakes, iron oxides, titanium dioxide, natural colors or pearlescent pigments (e.g. mica based pigments sold under the Candurin trade name). Examples of such pigments are listed in U.S. Pat. No. 4,543,570, which is incorporated herein by reference. When included, the pigments may be used in the powder mixtures in a range (by weight) from about greater than 0 to about 40% pigment, preferably, from about 4 to about 32% and, more preferably, from about 7 to about 30%. It will be understood, however, that the amount of pigment employed in the powder mixtures of the invention is an amount which is sufficient or effective to impart the required appearance of the outer coating to the surface of the substrate to be coated.

Furthermore, the powder mixtures may also include supplemental or auxiliary ingredients typically found in film coatings. A non-limiting list of such adjuvants includes surfactants, suspension aids, sweeteners, flavorants, etc. and mixtures thereof. A preferred surfactant is sodium lauryl sulfate. When included, the surfactant is in the range of about 0.1 to about 7% in the dry film coating composition, and, more preferably between about 1 to about 4%. The use and function of the surfactant is to enhance the film formation process as commonly taught and used in the prior art.

The powder mixtures are prepared using standard dry blending or mixing techniques known to those of ordinary skill. For example, the ingredients are individually weighed, added to a suitable apparatus and blended for a sufficient time until a substantially uniform mixture of the ingredients is obtained. The time required to achieve such substantial uniformity will, of course, depend upon the batch size and apparatus used. If any of the powder formulation ingredients are liquids, they are added only after all of the dry ingredients have been sufficiently blended, and the combination of wet and dry ingredients is blended for an additional amount of time to ensure homogeneity once all of the liquid is introduced.

As mentioned above, batch sizes will vary upon need. A non-limiting list of suitable blending devices include diffusion blenders such as a cross flow, V-blender, or hub blender, available from Patterson-Kelly, or convection blenders, such as Ruberg or CVM blenders, available from Azo and Readco, respectively, may be used. Blending of the aforementioned formulations may also be achieved by processing ingredients into a granular form to produce a non-dusting granular coating composition by methods including, but not limited to, wet massing, fluid bed granulation, spray granulation and dry compaction, roller compaction or slugging Other manners of blending will be apparent to those of ordinary skill.

Some preferred dry film coating compositions in accordance with the present invention include:

| Ingredient | % by weight | Preferred | More Preferred |
|---|---|---|---|
| Polymer e.g. PVA | 20-80 | 25-60 | 30-50 |
| Waxy detackifier_e.g. gms, etc with mps = <150 microns | 1-30 | 2-15 | 4-10 |
| Glidant (when present) e.g. talc, etc. | 9-50 | 12-40 | 15-30 |
| Surfactant (when present) e.g. Na lauryl sulfate, etc. | 0.1-7 | 1-4 | — |
| Plasticizers (when present) PEG, TEC, etc. | 1-25 | 2-20 | 4-15 |
| Pigments | 0-40 | 4-32 | 7-30 |
| Optional or aux. ingredients | 0-20 | — | — |

It will be understood from the foregoing table that the preferred dry film coating compositions will include at least a polymer and a waxy detackifier as described herein. The additional ingredients, if included, will cause the amount of polymer and a waxy detackifier to be reduced proportionally but still within the ranges described herein so that the total amount of all ingredients in the dry blend will be 100% by weight.

For purposes of illustration and not limitation, an aqueous dispersion having about 20% solids content can be formed by dispersing 80 grams of a blended powder mixture described hereinabove into 320 grams of ambient temperature water. The water is weighed into a suitable vessel, i.e. one with a diameter approximately equal to the depth of the final suspension. A low shear mixer, preferably one having a mixing blade with a diameter about one third the diameter of the mixing vessel, is lowered into the water and turned on to create a vortex from the edge of the vessel down to about just above the mixing blade to prevent entrapment of air. The 80 grams of dry film coating composition is added to the vortex at a rate where there is no excessive build up of dry powder. The speed and depth of the mixing blade is adjusted to avoid air being drawn into the suspension so as to avoid foaming. The suspension is stirred at low speed, preferably 350 rpm or less, for a time sufficient to ensure that a homogenous mixture is formed. Using the above batch size as a guide, about 45 minutes mixing time is required. The suspension is then ready for spraying onto pharmaceutical substrates and the like. Those of ordinary skill will also realize that there are many ways of preparing a substantially homogenous mixture of the solids in water and that the scope of the invention is in no way dependent on the apparatus used.

In still further embodiments of the invention, there are provided orally-ingestible substrates coated with the inventive film coating formulations. The coated substrates have excellent appearance and uniformity as well as enhanced stability in the presence of environmental moisture and oxygen.

As will be described in the examples below, the methods in accordance with the present invention include applying the film coating compositions as described herein as aqueous suspensions to the surfaces of orally ingestible substrates. The film coating can be applied as part of a pan coating or spray coating process commonly used to coat such articles. The amount of coating applied will depend upon several factors, including the nature and functionality of the film coating, the substrate to be coated and the apparatus employed to apply the coating, etc. In some immediate release applications of the invention, the substrates will be tablets and will be coated to a theoretical weight gain of from about 0.25 to about 5.0%. Preferably, the theoretical weight gain is from about 0.5 to about 4.0% and more preferably, the theoretical weight gain is from about 1.0 to about 3.0% by weight of said substrate. For coatings which function as enteric coatings, a more desirable weight gain would be a theoretical weight gain of between about 6 and about 12%, and more preferably between about 8 and about 10%. As mentioned above, the coating solutions of the present invention may also include auxiliary ingredients in addition to the powder mixture and the water.

The coated, orally-ingestible substrates described above can also include a subcoat film coating between the orally-ingestible substrate and the inventive film coating comprising a fine particle size detackifier. The subcoat selected is preferably based on an edible film coating composition that is compatible with and adheres to both the orally-ingestible substrate and the inventive coating. Thus, the artisan may choose from a wide variety of pharmaceutical or food-acceptable coatings for use as subcoats in the present invention. The subcoat is also applied to the substrate to provide from about a 0.25 to about a 5.0% weight gain to the orally-ingestible substrate.

Regardless of the method employed or the specific materials included in the film coating compositions, the orally-ingestible substrates of the present invention will include a film coating having a fine particle size waxy detackifier which has a median particle size of less than about 150 microns, preferably less than about 100 microns and most preferably less than about 50 microns.

A non-limiting list of suitable substrates that can be coated with the inventive coating system include compressed tablets, caplets, cores including pharmaceuticals, nutraceuticals and dietary supplements as well as any other art-recognized orally ingestible core.

5. EXAMPLES

The following examples serve to provide further appreciation of the invention but are not meant in any way to restrict the effective scope of the invention. All ingredients are expressed as being by weight %.

Example 1

A summary of the particle size values of selected detackifiers are presented in the following table:

| Detackifier | Particle Size (microns) d (0.5) | Particle Size (microns) d (0.9) |
|---|---|---|
| Stearoyl polyoxylglycerides (Gelucire 50/13) - spray cooled | 29.8 | 103.9 |
| Glyceryl monostearate (GMS) - spray cooled | 32.5 | 90.8 |
| Glyceryl palmitostearate (Precirol ATO 5) - spray cooled | 29.7 | 63.9 |
| Glyceryl behenate (Compritol 888 ATO) - spray cooled | 39.9 | 90.4 |
| Self-emulsifying (SE) glyceryl monostearate Imwitor (Sasol) 960P - standard | 298.3 | 880.6 |
| Glyceryl monostearate Imwitor (Sasol) 900K - standard | 374.6 | 1212.3 |

In each case, the powder to be tested was placed in a Malvern Mastersizer 2000 configured for powder analysis, and the vibratory feed rate was adjusted to provide an obscuration value of less than 6%, which correlates to greater than 94% of the measured laser response for particle size characterization. The above conditions were optimized, and particle size distributions were determined using a dispersion pressure of 4 bar to ensure adequate dispersion of particles and consistent results. Median particle size values, represented as d (0.5), were then reported by the instrument. Median particle size d (0.5) means that 50 volume % of the particles were less than the reported value. A d (0.9) particle size value was also reported. The d (0.9) value indicates that 90 volume % of the particles were less than the reported value. The results above indicate that the median particle sizes, d (0.5), for the preferred fine particle size detackifiers are typically less than 50 microns; whereas, the SE-GMS 960P and Sasol GMS 900K have median particle sizes of 298.3 and 374.6 microns, respectively. In addition, the preferred fine particle size detackifiers have d (0.9) values of not more than 250 microns.

Example 2

A preferred formulation for an inventive dry coating composition is the following:

| Component | Percent | grams |
|---|---|---|
| PVA copolymer* | 35.00 | 28.00 |
| Talc | 27.00 | 21.60 |
| Glyceryl monostearate [d (0.5) = 32.5 microns] | 4.50 | 3.60 |
| Triethyl citrate | 6.00 | 4.80 |
| Sodium lauryl sulfate | 2.50 | 2.00 |
| Titanium dioxide | 20.00 | 16.00 |
| Blue #2 lake | 5.00 | 4.00 |
| | 100.00 | 80.00 |

*(80% PVA:17.5% methyl methacrylate:2.5% acrylic acid)

Preparation of the Dry Film Coating Composition:

The dry film coating composition was prepared by adding all dry ingredients (PVA copolymer, talc, glyceryl monostearate with median particle size of 32.5 microns, sodium lauryl sulfate, titanium dioxide and blue#2 lake) into a laboratory blender and blending for 5 minutes until a homogenous mixture was produced. Methyl citrate, the only liquid component, was then gradually added to the dry mixture, and the total mixture was blended for an additional 5 minutes after all liquid was introduced.

Preparation of the Aqueous Dispersion:

The dry film coating composition (80 grams) was dispersed into 320 grams of ambient temperature water to make an aqueous coating suspension having 20% w/w non-water ingredients. The water was weighed into a vessel with a diameter approximately equal to the depth of the final dispersion. A low shear mixer was lowered into the water and turned on to create a vortex from the edge of the vessel down to just above the mixing blade to prevent entrapment of air. The 80 grams of dry film coating composition was added to the vortex at a rate where there was no excessive build up of dry powder. The speed and depth of the mixing blade was adjusted to avoid air being drawn into the suspension so as to avoid foaming. The suspension was stirred at low speed (350 rpm or less) for 45 minutes to form a homogeneous aqueous dispersion suitable for coating.

Coating of Tablets:

A 1.5 kilogram batch of convex placebo tablets (10 mm diameter) was spray coated with the aqueous dispersion described above in an O'Hara LabCoat fully perforated side-vented coating pan equipped with a pan insert having a diameter of 15" and one spray gun fitted with a nozzle having an aperture of 1 mm. The average coating parameters were: inlet temperature (IT) 65° C., exhaust temperature (ET) 48° C., coating bed temperature (BT) 45° C., airflow 250 cubic meters/hr, air pressure −0.1 in. of water, atomizing air pressure (AP) 1.5 bar, pan speed (PS) 22 rpm. A theoretical coating weight gain of 3.0% was applied to the tablets. The resulting coated tablets were smooth, non-tacky and glossy.

Determination of Maximum Fluid Delivery Rate:

During the coating process described above, the fluid delivery rate (FDR) was gradually increased until the point where tablets were observed to complete a full revolution stuck to the surface of the pan. At this point, the spray rate was reduced to obtain a rate at which the tablets did not stick to the pan, and this spray rate was recorded as the maximum fluid delivery rate. The maximum fluid delivery rate for Example 2 was determined to be 32 g/min.

Determination of Water Vapor Transmission Rate:

Water vapor transmission rate (WVTR) (also known as Moisture Vapor Transmission rate, MVTR) was determined by first preparing a cast film sample from the aqueous dispersion described above by sequentially applying the dispersion onto a flat polyethylene terephthalate (PET) surface and then drying in a laboratory oven at 40° C. A 100 micron thick film was thus obtained for testing. WVTR of the film was measured on a VTI WPA-100 unit. The unit was set for an initial drying phase, where the sample was purged at 25° C. and 100 cc/min (dry N2) for 15 min, and then one side of the sample was flushed with nitrogen gas at 25° C./80% RH at a rate of 200 cc/min until a stable WVTR was determined through the sample. The WVTR of Example 2 was determined to be 5 g water/day/100 inches$^2$.

Examples 3-11

Additional Film coating compositions (80 grams, each) and aqueous dispersions comprising them in accordance with the present invention were prepared by methods identical to those described in Example 2. Maximum fluid delivery rates and gun blockages were determined. In particular examples, the MVTR was determined.

| | Example | | | | |
|---|---|---|---|---|---|
| | 3 % | 4 % | 5 % | 6 % | 7 % |
| Component | | | | | |
| PVA Copolymer* | 35 | 35 | 35 | 40 | 40 |
| Talc | 27 | 27 | 27 | 22 | 24 |
| Titanium dioxide | 25 | 25 | 25 | 25 | 25 |
| Triethyl citrate | 6 | 6 | 6 | 8 | 8 |
| Sodium lauryl sulfate | 2.5 | 2.5 | 2.5 | 2 | |
| Stearoyl polyoxylglyceride (Gelucire 50/13) [d (0.5) = 29.8 microns] | 4.5 | | | | |
| Glyceryl behenate (Compritol 888 ATO) [d (0.5) = 39.9 microns] | | 4.5 | | | |
| Glyceryl palmitostearate (Precirol ATO 5) [d (0.5) = 29.7 microns] | | | 4.5 | | |
| Glyceryl monostearate [d (0.5) = 32.5 microns] | | | | 3 | 3 |
| Totals | 100 | 100 | 100 | 100 | 100 |
| Performance | | | | | |
| Max spray rate (g/min) 15" insert | 28 | 20 | 18 | 30 | 30 |
| Gun blockages | 0 | 0 | 0 | 0 | 0 |
| Water vapor transmission rate (g water/day/100 in$^2$) | 6.6 | 9.1 | 5.9 | n.d. | n.d. |

| | Example | | | |
|---|---|---|---|---|
| | 8 % | 9 % | 10 % | 11 % |
| Component | | | | |
| PVA | 35 | 42.6 | 41 | 35.5 |
| Talc | 27 | 17.4 | 16 | 14.5 |
| Titanium dioxide | 25 | 25 | 23 | 25 |
| Blue #2 lake | | 5 | 5 | 5 |
| Triethyl citrate | 6 | | | |
| Glyceryl monostearate [d (0.5) = 32.5 microns] | 4.5 | | | |
| Stearoyl polyoxyglyceride (Gelucire 50/13) [d (0.5) = 29.8 microns] | | 10 | 15 | 20 |
| Sodium lauryl sulfate | 2.5 | | | |
| Totals | 100 | 100 | 100 | 100 |
| Performance | | | | |
| Max spray rate (g/min) 15" insert | 32 | 27 | 32 | 36 |
| Gun blockages | 0 | 0 | 0 | 0 | n.d. = not determined
*(80% PVA:17.5% methyl methacrylate:2.5% acrylic acid)

Examples 3-11 demonstrate that a range of different fine particle size materials can perform as detackifiers in PVA copolymer and PVA formulations, with fine particle size GMS and Gelucire 50/13 providing the two highest values of maximum fluid delivery rate. In Examples 6 and 7, it is shown that identical maximum fluid delivery rates can be obtained whether sodium lauryl sulfate is included in the formulation or not. In Examples 9-11, it was determined that higher inclusion levels of Gelucire 50/13 can lead to increased maximum fluid delivery rates for PVA based film coating formulations.

Comparison to Prior Art

To provide evidence that the enhanced barrier and maximum fluid delivery rate of the inventive formulations of this disclosure are superior and preferred over the prior art, a series of evaluations were conducted on both prior art and instant film coating formulations. These evaluations and their methods are described in detail below.

Comparative Example A

WO2006111981 Example 4

The composition from Example 4 of WO2006111981 was prepared as described in hot water (~75° C.) as required by the teachings therein and film coated in an O'Hara LabCoat, equipped with a 15" insert, using the same substrates and conditions as described in Example 2 of this document. Sasol Imwitor SE-GMS as indicated in the '981 PCT application was used in this formulation.

Comparative Example B

The composition from Example 4 of the '981 PCT application was attempted to be dispersed in ambient water to determine its suitability for preparation in this way and film coated in an O'Hara LabCoat, equipped with a 15" insert, using the same substrates and conditions as described in Example 2 hereinabove. Sasol Imwitor SE-GMS as indicated in the '981 PCT application was also used in this formulation.

Example 12

Inventive

A similar formulation was utilized as in Comparative Example B except that the Sasol Imwitor SE-GMS was replaced by fine particle size GMS, d(0.5)=32.5. The aqueous dispersion and coating process was then conducted in the manner described in Example 2 hereinabove.

The formulations and results corresponding to Comparative Examples A-B and Example 12 (inventive) are reported in the following table.

|  | Comparative Example | | |
|---|---|---|---|
|  | Comparative Example A % | Comparative Example B % | Example 12 % |
| Component |  |  |  |
| Polyvinyl alcohol | 44 | 44 | 44 |
| Self Emulsifying GMS Sasol Imwitor 960P | 22 | 22 |  |
| Glyceryl monostearate [d (0.5) = 32.5 microns] |  |  | 22 |
| Titanium dioxide | 26 | 26 | 26 |
| Triethyl citrate | 8 | 8 | 8 |
| Totals | 100 | 100 | 100 |
| Aqueous dispersion temperature (° C.) | 75 | 21 | 21 |
| Performance |  |  |  |
| Max spray rate (g/min) 15" insert | 30 | 0 | 38 |
| Gun blockages | 0 | continuous | 0 |

It is apparent from the above result that the use of a fine particle size grade of glyceryl monostearate enables dispersion in ambient temperature water and also enhances the productivity of the formulation over that described in the prior art.

Comparative Examples C, D and E

These comparative formulations were prepared according to the methods of Example 2 hereinabove except that the fine particle sized detackifier of Example 2 was replaced with the detackifier as shown in the tables below.

|  | Example 8 restated % | Comparative Example C % | Comparative Example D % |
|---|---|---|---|
| Component |  |  |  |
| PVA | 35 | 35 | 35 |
| Talc | 27 | 27 | 27 |
| TiO$_2$ | 25 | 25 | 25 |
| Triethyl citrate | 6 | 6 | 6 |
| Sodium lauryl sulfate | 2.5 | 2.5 | 2.5 |
| Glyceryl monostearate [d (0.5) = 32.5 microns] | 4.5 |  |  |
| Sasol SE-GMS 960P |  | 4.5 |  |
| Sasol Imwitor 900K |  |  | 4.5 |
| Totals | 100 | 100 | 100 |
| Performance |  |  |  |
| Max spray rate (g/min) 15" insert | 32 | 24 | 26 |
| Gun blockages | 0 | several | several |

A similar observation was found when PVA copolymer was substituted for PVA.

|  | Example 2 restated % | Comparative Example E % |
|---|---|---|
| Component |  |  |
| PVA copolymer* | 35 | 35 |
| Talc | 27 | 27 |
| Titanium dioxide | 25 | 25 |
| Triethyl citrate | 6 | 6 |
| Sodium lauryl sulfate | 2.5 | 2.5 |
| Glyceryl monostearate [d (0.5) = 32.5 microns] | 4.5 |  |
| Sasol SE-GMS 960P |  | 4.5 |
| Totals | 100 | 100 |
| Performance |  |  |
| Max spray rate (g/min) 15" insert | 30 | 26 |
| Gun blockages | 0 | several |

*(80% PVA:17.5% methyl methacrylate:2:5% acrylic acid)

Based on the above findings, it is apparent that the use of a fine particle size grade of glyceryl monostearate demonstrated advantages over the self-emulsifying glyceryl monostearate described in the '981 application and provides a reliable film coating formulation, dispersible in ambient temperature water, with good productivity that does not necessarily need to include a surfactant.

Comparative Example F

Opadry® H Systems of U.S. Pat. No. 6,448,323

A formulation disclosed in the '323 patent was dispersed in water and coated onto tablets in an O'Hara LabCoat equipped with a 15" insert using the conditions as described in Example 2 hereinabove. The formula details and coating performance are provided as Comparative Example F. The maximum fluid delivery rate of this formulation was determined to be 29 g/min, and the water vapor transmission rate for the film 13.5 g $H_2O$/day/100 inches square. It is apparent from the examples herein that the inventive compositions lead to excellent maximum fluid delivery rates, comparable to those of the formulations disclosed in the '323 patent, and also, desirably, decreased moisture vapor transmission rates, i.e. preferably less than about 9 g $H_2O$/day/100 inches square when compared to those of compositions disclosed in the '323 patent.

Comparative Example G

Example 14 of U.S. Pat. No. 5,885,617

The composition of Example 14 of the '617 patent was dispersed in water and coated onto tablets in an O'Hara LabCoat equipped with a 15" insert as described in above Example 2. The maximum fluid delivery rate of this formulation was determined to be 11 g/min, and the water vapor transmission rate for the film 6.4 g $H_2O$/day/100 inches square. It is apparent from the inventive examples herein that the compositions in accordance with the invention lead to substantially increased maximum fluid delivery rates i.e. 30 g/min or higher with PVA-based systems and also equivalent or substantially similar moisture vapor transmission rates when compared to those associated with the film coating compositions disclosed in the '617 patent.

| Component | Comparative Example F % | Comparative Example G % |
|---|---|---|
| Polyvinyl alcohol | 40 | 45.52 |
| Titanium dioxide | 25 | 32 |
| Polyethylene glycol | 20.2 | |
| Talc | 14.8 | 20 |
| Xanthan gum | | 0.48 |
| Soya lecithin | | 2.0 |
| Totals | 100 | 100 |
| Performance | | |
| Max spray rate (g/min) 15" insert | 29 | 11 |
| Gun blockages | 0 | 0 |
| Water vapor transmission rate (g water/day/100 in²) | 13.5 | 6.4 |

Example 13

The products and procedures of Example 2 are repeated except that hypromellose is used to replace the PVA copolymer.

Examples 14-15

The products and procedures of Example 2 are repeated except that stearic acid, having a median particle size of about 50 microns (Ex. 14) and about 100 microns (Ex. 15) are used respectively to replace the glyceryl monostearate.

Example 16

The procedures of Example 2 are repeated using the materials shown in the table below and the coating conditions are modified such that the inlet air temperature is reduced to provide a tablet bed temperature of 30° C.

| | Example 16 % | Comparative Example H % |
|---|---|---|
| Component | | |
| Poly(methacrylic acid, ethyl acrylate) 1:1 (Eudragit L100-55) | 64.49 | 60 |
| Talc | 14.1 | 29.25 |
| Triethyl citrate | 7.73 | 7.2 |
| Sodium bicarbonate | 1.93 | 1.8 |
| Colloidal silicon dioxide | 1.25 | 1.25 |
| Sodium lauryl sulfate | 0.5 | 0.5 |
| Glyceryl monostearate [d (0.5) = 32.5 microns] | 10 | |
| Totals | 100 | 100 |
| Performance | | |
| Max spray rate (g/min) 15" insert | 20 | 16 |
| Gun blockages | 0 | 0 |

It is apparent from the above results that the use of a fine particle size grade of glyceryl monostearate enables dispersion of the acrylic polymer film coating composition in ambient temperature water and also offers the opportunity to significantly reduce the level of talc in the formulation while actually improving the coating productivity over that described in the prior art.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A dry film coating composition comprising a) a polymer selected from the group consisting of polyvinyl alcohol, polyvinyl alcohol comprising partially hydrolyzed polyvinyl acetate having a percentage of hydrolysis greater than about 86.5 mol %, polyvinyl alcohol copolymers comprising partially hydrolyzed polyvinyl acetate having a percentage of hydrolysis greater than about 86.5 mol % onto which has been graft polymerized methyl methacrylate and acrylic acid to give a ratio of PVA-methyl methacrylate-acrylic acid moieties of 80:17.5:2.5, hypromellose (hydroxypropylmethyl cellulose), hydroxypropyl cellulose, sodium carboxymethyl cellulose and mixtures thereof, and b) a waxy detackifier having a median particle size of less than 150 microns selected from the group consisting of glyceryl monostearate, stearoyl polyoxylglycerides, glyceryl behenate, glyceryl palmitostearate and mixtures thereof.

2. The composition of claim 1 wherein the waxy detackifier has a median particle size of less than 100 microns.

3. The composition of claim 1 wherein the waxy detackifier has a median particle size of less than 50 microns.

4. The composition of claim 1 further comprising one or more of a plasticizer, a glidant, a pigment and a surfactant.

5. The composition of claim 4 wherein the plasticizer is triethyl citrate.

6. The composition of claim 4 wherein the surfactant is sodium lauryl sulfate.

7. The composition of claim 4 wherein the glidant is talc.

8. The composition of claim 1 wherein the polyvinyl alcohol or polyvinyl alcohol copolymer comprises 20-70% by weight of the total composition.

9. The composition of claim 4 wherein the plasticizer is triethyl citrate, the detackifier is glyceryl monostearate, and the surfactant is sodium lauryl sulfate.

10. The composition of claim 1 wherein the waxy detackifier comprises from about 1 to about 30% by weight of the total composition.

11. The composition of claim 10 wherein the waxy detackifier comprises from about 2 to about 15% by weight of the total composition.

12. The composition of claim 11 wherein the waxy detackifier comprises from about 4 to about 10% by weight of the total composition.

13. The composition of claim 4 wherein the glidant comprises 9-50% by weight of the total composition.

14. An aqueous suspension prepared by mixing the composition of claim 1 in water.

15. An orally-ingestible substrate coated with the aqueous suspension of claim 14.

16. A pharmaceutically acceptable oral dosage form, comprising an orally-ingestible substrate, coated with a film coating containing a) a polymer selected from the group consisting of polyvinyl alcohol, polyvinyl alcohol comprising partially hydrolyzed polyvinyl acetate having a percentage of hydrolysis greater than about 86.5 mol %, polyvinyl alcohol copolymers comprising partially hydrolyzed polyvinyl acetate having a percentage of hydrolysis greater than about 86.5 mol % onto which has been graft polymerized methyl methacrylate and acrylic acid to give a ratio of PVA-methyl methacrylate-acrylic acid moieties of 80:17.5:2.5, hypromellose (hydroxypropylmethyl cellulose), hydroxypropyl cellulose, sodium carboxymethyl cellulose and mixtures thereof, and b) a waxy detackifier having a median particle size of less than 150 microns selected from the group consisting of glyceryl monostearate, stearoyl polyoxyglycerides, glyceryl behenate, glyceryl palmitostearate and mixtures thereof.

17. The pharmaceutically acceptable oral dosage form of claim 16, wherein the film coating has a water vapor transmission rate of less than about 9 g $H_2O$/day/100 inches square.

18. The composition of claim 1, wherein the immediate release polymer is polyvinyl alcohol.

19. A dry, immediate release film coating composition comprising a) 20-70% by weight of a polymer selected from the group consisting of polyvinyl alcohol, polyvinyl alcohol comprising partially hydrolyzed polyvinyl acetate having a percentage of hydrolysis greater than about 86.5 mol %, polyvinyl alcohol copolymers comprising partially hydrolyzed polyvinyl acetate having a percentage of hydrolysis greater than about 86.5 mol % onto which has been graft polymerized methyl methacrylate and acrylic acid to give a ratio of PVA-methyl methacrylate-acrylic acid moieties of 80:17.5:2.5, hypromellose (hydroxypropylmethyl cellulose), hydroxypropyl cellulose, sodium carboxymethyl cellulose and mixtures thereof; b) 1 to 30% by weight of a detackifier comprising spray cooled glyceryl monostearate having a median particle size of less than 150 microns; c) 9-50% by weight of a glidant; d) plasticizer; and e) a surfactant.

* * * * *